(12) United States Patent
Kringel et al.

(10) Patent No.: US 6,251,117 B1
(45) Date of Patent: Jun. 26, 2001

(54) VASCULAR CLIP

(75) Inventors: Bernd Kringel, Fridingen; Theodor Lutze; Lothar Schutzbach, both of Balgheim, all of (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/654,427

(22) Filed: Sep. 1, 2000

Related U.S. Application Data

(63) Continuation of application No. PCT/EP99/00544, filed on Jan. 28, 1999.

(30) Foreign Application Priority Data

Mar. 4, 1998 (DE) ................................................ 198 09 121

(51) Int. Cl.⁷ .................................................. A61B 17/00
(52) U.S. Cl. ............................................................ 606/158
(58) Field of Search .................................. 606/157, 158, 606/151, 142, 143, 138, 139

(56) References Cited

U.S. PATENT DOCUMENTS

| | | |
|---|---|---|
| 1,837,277 | 12/1931 | Lund . |
| 4,192,315 | 3/1980 | Hilzinger et al. . |
| 4,360,023 | 11/1982 | Sugita et al. . |
| 4,484,581 | 11/1984 | Martin et al. . |
| 4,765,335 | 8/1988 | Schmidt et al. . |
| 5,312,426 | * 5/1994 | Segawa et al. ...................... 606/158 |

FOREIGN PATENT DOCUMENTS

| | | |
|---|---|---|
| 26 58 478 | 4/1978 | (DE) . |
| 31 39 488 | 4/1983 | (DE) . |
| 37 22 311 | 1/1989 | (DE) . |
| 297 08 218 U | 8/1997 | (DE) . |
| 0 346 084 | 12/1989 | (EP) . |

\* cited by examiner

Primary Examiner—Gary Jackson
Assistant Examiner—Vikki Hoa Trinh
(74) Attorney, Agent, or Firm—Barry R. Lipsitz

(57) ABSTRACT

In order to provide better guidance for the two branches in the region of a cross-over point of a vascular clip having a first and a second branch which are pivotal resiliently into a closed position whereby, in the region of the cross-over point, the first branch passes through a longitudinal slot in the second branch formed between two parallel webs, it is proposed that a bridge piece be arranged laterally of the first branch which passes through the second branch, and that the bridge piece extends in parallel with the section passing through the longitudinal slot in the second branch and, together with the section passing through the longitudinal slot in the second branch, forms a longitudinal slot which is closed at each side and into which a web of the second branch is guided.

7 Claims, 3 Drawing Sheets

Figure 1:
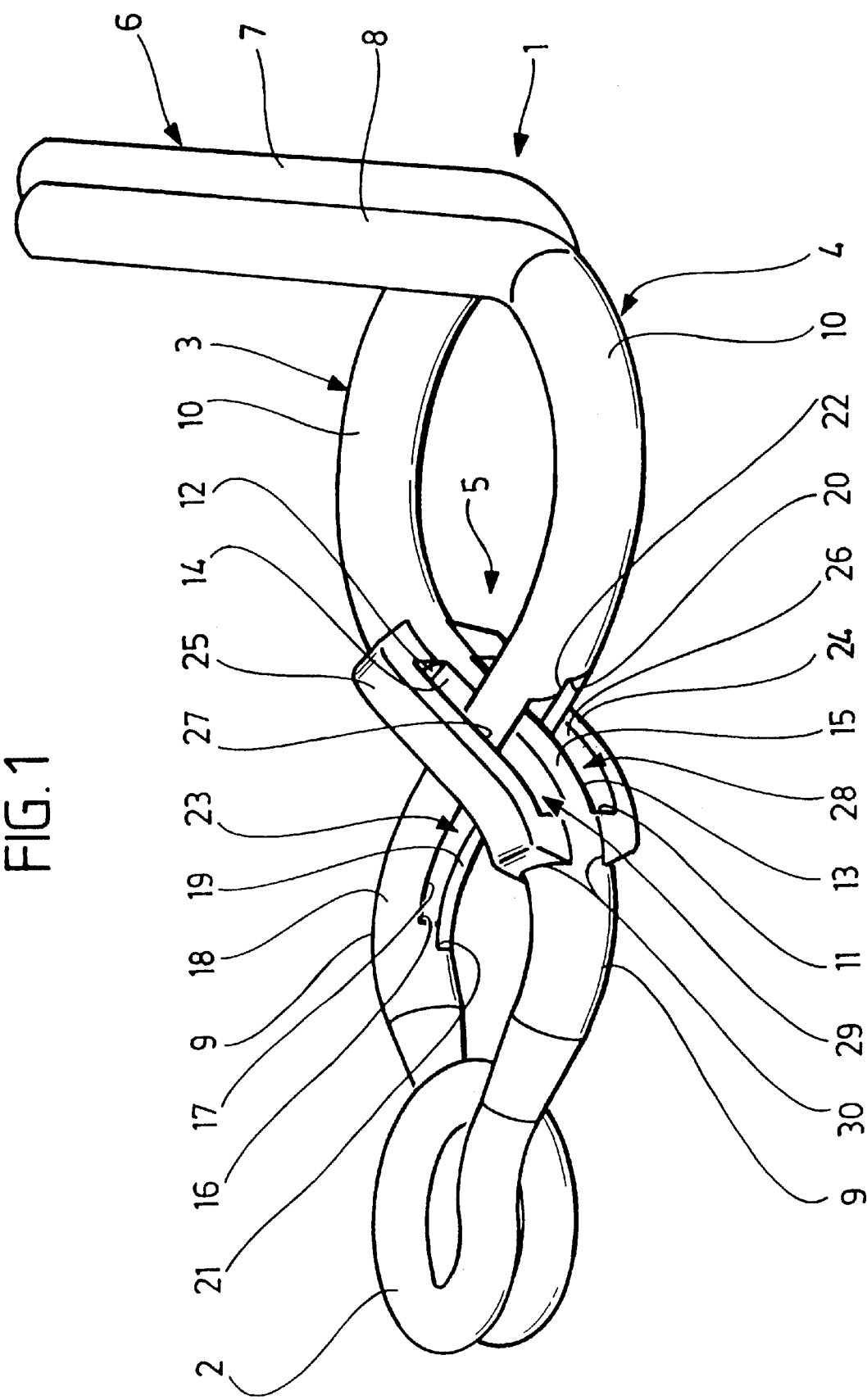

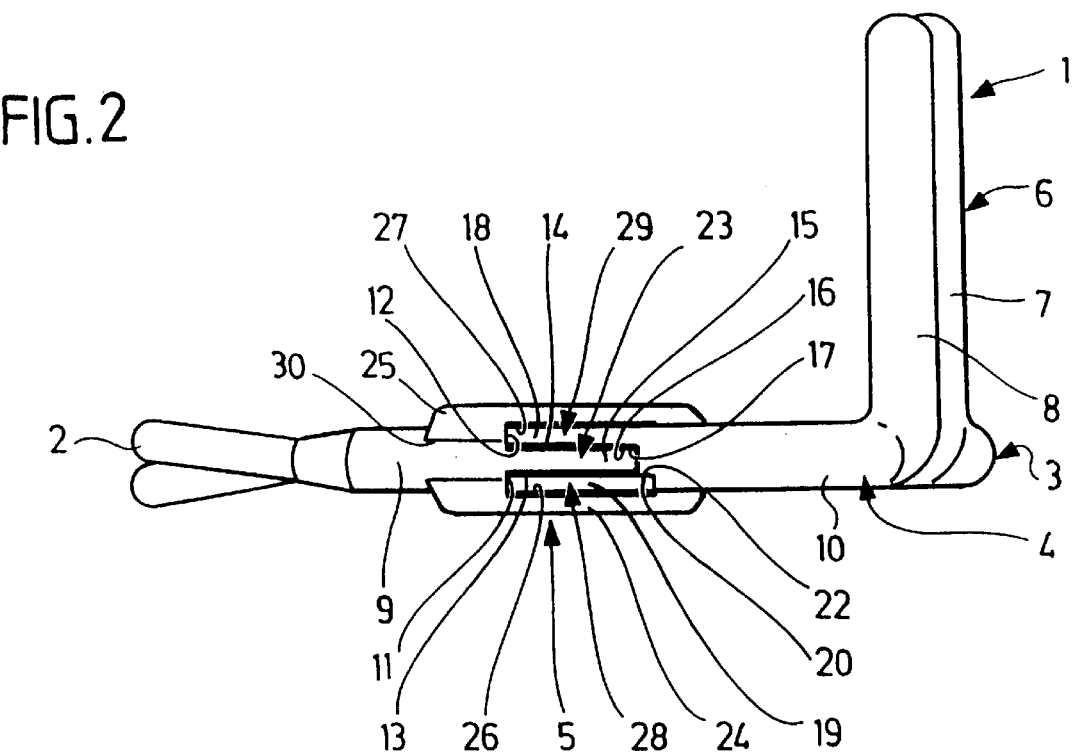
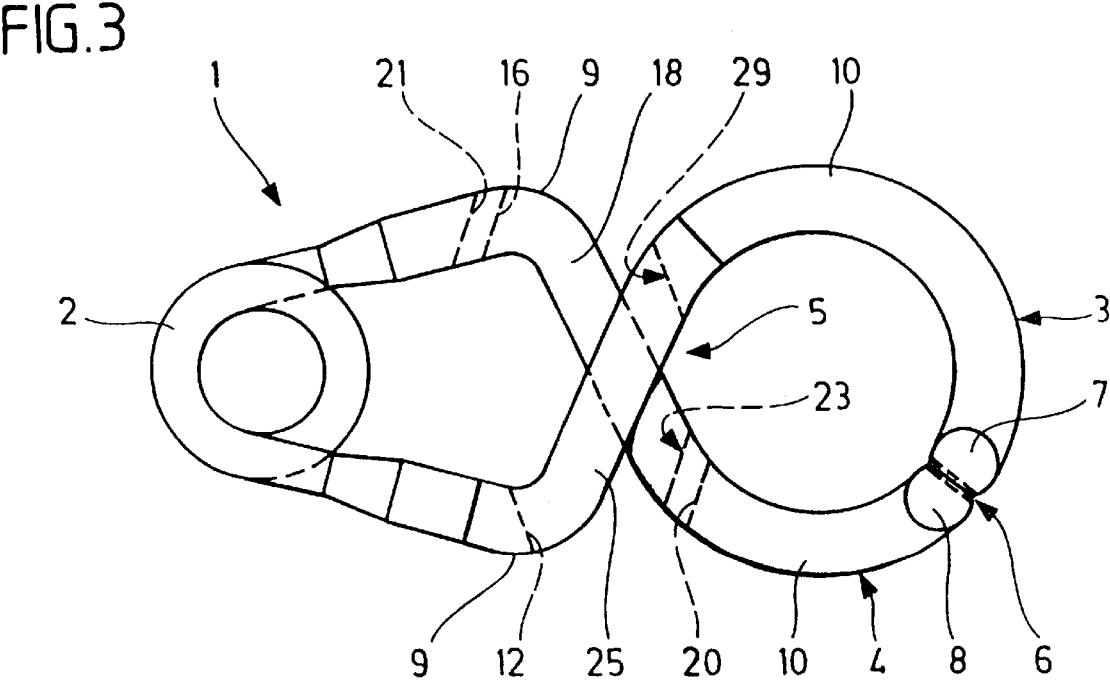

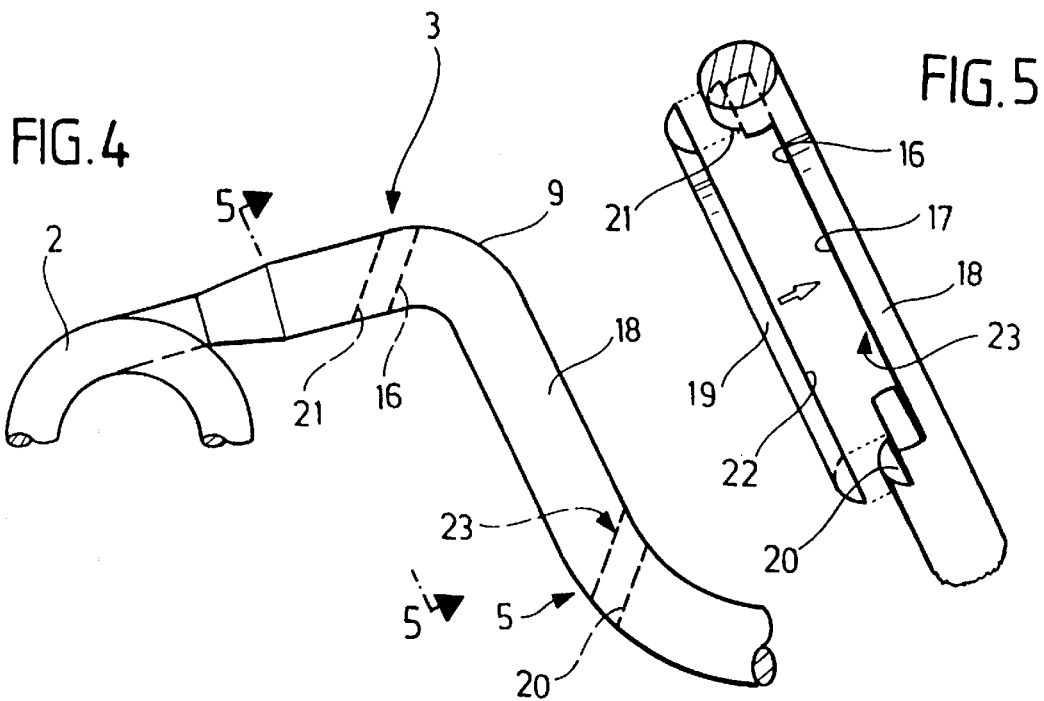
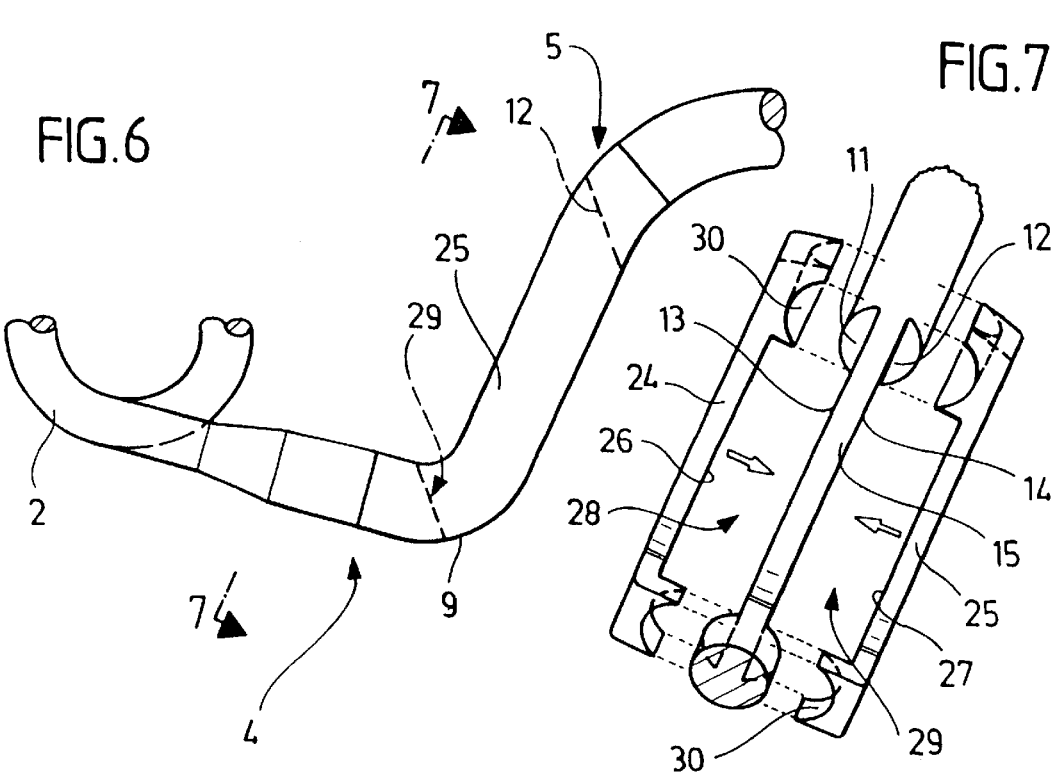

VASCULAR CLIP

This application is a continuation of PCT/EP99/00544 filed on Jan. 28, 1999. The present invention relates to the subject matter disclosed in international application PCT/EP 99/00544 of Jan. 28, 1999, the entire specification of which is incorporated herein by reference.

The invention relates to a vascular clip having a first and a second branch which are pivotal resiliently into a closed position whereby, in the region of a cross-over point, the first branch passes through a longitudinal slot in the second branch formed between two parallel webs.

Vascular clips of this type are employed for firmly clamping aneurysms in blood vessels for example. It is known thereby, to bend the substantially one-piece vascular clips which are made of a resilient round material in such a manner that the two ends of this round material form two branches which press together the clamping-cheeks located at their free ends in a resilient manner. For the purposes of guiding the two branches relative to one another, the two branches cross over and, in the region where they cross, this relative guidance is provided by feeding the first branch through a longitudinal slot in the second branch. In order to enhance the guidance arrangement, it is known to flatten the round material of the first branch on each side so that the flattened side-faces of the first branch will rest in planar manner on the likewise flattened inner surfaces of the longitudinal slot in the second branch. The longitudinal slot thus forms a guide box or enclosure box in which the double-sided flattened central region of the first branch can be guided in planar manner.

It has become apparent that this guidance arrangement is not quite sufficient when vascular clips of this type are subjected to extreme loads. Namely, there is a danger that a torsional force will nevertheless be applied to the first branch in the region of this guidance arrangement, possibly caused by the material of the first branch itself twisting or as the result of a very small widening of the enclosure box.

The object of the invention is to design a vascular clip in accordance with the first part of the main Claim such that torsion in the branches and hence lateral divergence of the clamping-cheeks can be prevented even under extreme loads.

In accordance with the invention, this object is achieved in the case of a vascular clip of the type described hereinabove in that a bridge piece is arranged laterally of the first branch which passes through the second branch, whereby said bridge piece extends in parallel with the section passing through the longitudinal slot in the second branch and, together with said section passing through the longitudinal slot, forms a longitudinal slot which is closed at each side and into which a web of the second branch is guided.

By virtue of this construction, a second enclosure box is, in practice, thereby produced, this time namely, by means of the section passing through the longitudinal slot in the second branch on the one hand, and, by means of the bridge piece applied externally to the first branch on the other. This enclosure box accommodates a web of the second branch so that a double form of guidance arrangement is created in the region of the cross-over, that is to say, firstly by means of the section of the first branch passing through the longitudinal slot in the second branch, and secondly, by means of the web penetrating into the longitudinal slot in the first branch.

In another preferred embodiment, provision is even made for such types of bridge piece to be arranged on each side of and in parallel with the section of the first branch that passes through the longitudinal slot in the second branch whereby, together with this section, the bridge pieces each form a respective longitudinal slot which is closed at each side and into which a respective web of the second branch is guided. Thus, in this construction, three enclosure boxes are provided one above the other so that, on the one hand, the section passing through the second branch will be guided in the central enclosure box and, on the other hand, the two webs of the second branch will be guided in the two outer enclosure boxes of the first branch.

Provision may hereby be made for the bridge piece of the first branch to be connected to the first branch at each end by welding, soldering or adhesion for example.

It is also advantageous if the bridge piece of the first branch bridges over a depression in the first branch which accommodates a web of the second branch. The height of the vascular clip in the region of the closure is then very small since the webs enter this depression and the bridge piece bridging over the depression thus projects laterally at most only slightly beyond the contour of the vascular clip. The depression may in any case have a stepped construction so that the bridge piece will then be disposed within the contour of the vascular clip and will not project at all.

It is advantageous for the inner surface of the bridge piece on the first branch to be flat. Thus, in conjunction with a similar flat construction for the webs of the second branch as well as for the section of the first branch passing through the longitudinal slot in the second branch, a fully planar guidance arrangement of the two branches relative to one another will also be provided in the lateral enclosure box.

The following description of preferred embodiments of the invention will serve to provide a more detailed explanation when taken in conjunction with the drawing. Therein FIG. 1 shows a perspective view of a vascular clip having a triple arrangement of enclosure boxes;

FIG. 2 a side view of the vascular clip of FIG. 1;

FIG. 3 a top view of the vascular clip of FIG. 1;

FIG. 4 a top view of the cross-over region of the second branch;

FIG. 5 a sectional view along the line 5—5 of FIG. 4 including a web prior to its connection to the second branch;

FIG. 6 a top view of the cross-over region of the first branch and

FIG. 7 a sectional view along the line 7—7 including two bridge pieces prior to their placement on the first branch.

The vascular clip 1 illustrated in the drawing consists of a resilient round material which is bent so as to form a double coil 2 and two branches 3, 4 that are mutually resiliently pivotal. These two branches 3 and 4 are bent towards one another at an approximate right angle in the plane of the coil 2 so that the two branches 3 and 4 cross at a cross-over region 5. After the cross-over region 5, the branches 3 and 4 are bent towards one another in the form of a circle and meet each other frontally in a clamping region 6. Each of the branches 3 and 4 is provided with a distinct right angular bend in this clamping region 6 and they end in two clamping portions 7, 8 which abut one another and project perpendicularly from the plane of the coil 2 and the branches 3 and 4. The clamping portions 7, 8 are pressed resiliently together due to the spring effect of the coil 2 and they can only be separated from one another by a resilient deformation of the vascular clip 1.

The two branches 3 and 4 are guided relative to one another in the cross-over region 5. For this purpose, depressions 11, 12 are worked into the first branch 3 in the region of the angular bend 9 and the curved section 10 adjoining the clamping region 6, said depressions being worked in from above and below and having flat bases 13, 14 so that the first branch 3 is reduced in the cross-over region 5 to a double-sided flattened section 15 of substantially rectangular cross-section having a thickness of approximately one third the diameter of the vascular clip 1 (FIG. 7).

In a similar manner, the second branch 4 is provided with a single-sided depression 16 having a flat base 17 in the cross-over region 5, although this depression is approximately twice as deep as the depressions 11 and 12 so that the second branch 4 is reduced to a web 18 having a thickness of approximately one third the diameter of the second branch 4 in the cross-over region 5.

The central, double-sided flattened section 15 of the first branch 3 is inserted into the depression 16 in such a manner that the side face of the section 15 rests flatly on the base 17 of the depression 16.

The depression 16 in the second branch 4 is closed by a web 19 which bridges over the depression 16. This web is of similar cross-section to the web 18 and it engages with two lateral, recessed shoulders 20, 21 in the depression 16 in such a manner that its outer contour is flush with the outer contour of the second branch 4. The web 19 is connected to the second branch in this position, for example, by laser welding, electron beam welding, soldering, adhesion etc.

The web 19 is flattened on the side 22 thereof facing the base 17 and rests flatly on the double-sided flattened section 15 of the first branch 3, this section 15 thereby being guided in planar manner in the longitudinal slot 23 and said longitudinal slot 23 being bounded by the two webs 18 and 19.

The webs 18 and 19 of the second branch 4 thereby enter the depressions 11 and 12 of the first branch 3 and, for practical purposes, do not project above the outer contour of the first branch 3.

The depressions 11 and 12 of the embodiment illustrated are both bridged over by a respective web-like bridge piece 24, 25. These web-like bridge pieces 24, 25 have a respective flat inner surface 26 and 27 and are laid externally over the two depressions 11, 12 in such a manner that two parallel longitudinal slots 28 and 29, which accommodate the webs 18 and 19, are formed between their inner surfaces 26 and 27 and the outer faces of the section 15. In this position, the bridge pieces 24 and 25, which are longer than the depressions 11, 12, are fixed to the outer face of the first branch 3 in like manner, for example, by laser welding, electron beam welding, soldering, adhesion etc. To this end, provision may be made for the bridge pieces 24 and 25 to comprise bearing surfaces 30 at their ends which surround the round material of the second branch 4 over a certain peripheral region (FIG. 7), although provision could also be made for flattened portions of the bridge pieces 24 and 25 to rest on correspondingly flattened abutment portions of the second branch 4, this arrangement not being illustrated in the drawing however.

Thus, two further guides or enclosure boxes are made available due to these bridge pieces 24 and 25, said further guides extending in parallel with the longitudinal slot 23 which itself also forms such a guide or enclosure box.

As a result of this construction, one obtains a triple guide arrangement for the two branches 3 and 4 in the cross-over region 5 and so any danger of torsion and thus separation of the clamping portions 7, 8 is eliminated.

What is claimed is:

1. A vascular clip having a first and a second branch which are pivotal resiliently into a closed position, wherein at a cross-over point, the first branch passes through a longitudinal slot in the second branch formed between two parallel webs, wherein a bridge piece is arranged laterally on each side of the first branch which passes through the second branch and each said bridge piece extends in parallel with the section passing through the longitudinal slot in the second branch, wherein together with the section passing through the longitudinal slot in the second branch, each of said bridge pieces of said first branch forms a longitudinal slot which is closed at each side and into which a respective one of the parallel webs of the second branch is guided.

2. A vascular clip in accordance with claim 1, wherein the bridge pieces of the first branch are welded, soldered or adhered to the first branch at each end.

3. A vascular clip in accordance with claim 1, wherein the bridge pieces of the first branch bridge over a depression in the first branch which accommodates the webs of the second branch.

4. A vascular clip in accordance with claim 2, wherein the bridge pieces of the first branch bridge over a depression in the first branch which accommodates the webs of the second branch.

5. A vascular clip in accordance with claim 1, wherein the inner surface of the bridge piece on the first branch is flat.

6. A vascular clip in accordance with claim 2, wherein the inner surface of the bridge piece on the first branch is flat.

7. A vascular clip in accordance with claim 3, wherein the inner surface of the bridge piece on the first branch is flat.

* * * * *